United States Patent [19]
Gajar et al.

[11] Patent Number: 5,429,734
[45] Date of Patent: Jul. 4, 1995

[54] MONOLITHIC CAPILLARY ELECTROPHORETIC DEVICE

[75] Inventors: Stephanie A. Gajar, Washington, D.C.; Michael W. Geis, Acton, Mass.

[73] Assignee: Massachusetts Institute of Technology, Cambridge, Mass.

[21] Appl. No.: 135,068

[22] Filed: Oct. 12, 1993

[51] Int. Cl.⁶ .................................................. G25B 9/00
[52] U.S. Cl. ................... 204/299 R; 427/58; 427/125; 427/255; 427/255.4; 427/255.7; 156/657.1
[58] Field of Search ............ 204/299 R, 180.1; 427/255, 255.7, 255.4, 58, 123, 125; 156/657

[56] References Cited

U.S. PATENT DOCUMENTS

| | | |
|---|---|---|
| 4,893,509 | 1/1990 | MacIver et al. .............. 156/657 |
| 4,908,112 | 3/1990 | Pace ............................. 204/299 R |
| 5,092,972 | 3/1992 | Ghowsi ......................... 204/182.1 |

FOREIGN PATENT DOCUMENTS

0457748A1  11/1991  European Pat. Off. .

OTHER PUBLICATIONS

Lee et al. (1990) "Direct Control of the Electroosmosis in Capillary Zone Electrophoresis by Using an External Electric Field", *Anal. Chem.*, 62:1550–1552 (no month).
Manz et al. (1992) "Planar Chips Technology for Miniaturization and Integration of Separation Techniques into Monitoring Systems" (Capillary Electrophoresis on a Chip), *J. Chromatog.*, 593:253–258 (no month).
Li (1992) "Capillary Electrophoresis-principles, practice and applications", *J. Chromatog.*, 52:1–30, 55–139, 145–154, 398–540, 541–553 (no month).

*Primary Examiner*—John Niebling
*Assistant Examiner*—Edna Wong
*Attorney, Agent, or Firm*—Thomas J. Engellenner; Anthony A. Laurentano; Lahive & Cockfield

[57] ABSTRACT

A method and apparatus for separating ions in a liquid sample based on electrophoretic mobility. The device includes a buried channel formed upon a semiconductor wafer and surrounded by an insulating material. A matrix liquid is disposed in the channel and facilitates movement of ions through the channel. A voltage source applies a voltage between first and second electrodes mounted in first and second reservoirs, respectively. The first and second reservoirs are located at opposite ends of the channel, and hold the matrix liquid. The applied voltage generates an electric field along the length of the channel that pulls molecules that are introduced into the channel along the channel, such that molecules having one polarity are attracted to the first electrode, and molecules having a second polarity are attracted to the second electrode.

23 Claims, 2 Drawing Sheets

MONOLITHIC CAPILLARY ELECTROPHORETIC DEVICE

This invention was made with Government support under Contract Number F19628-90-C-0002 awarded by the Air Force. The Government has certain rights in the invention.

BACKGROUND OF THE INVENTION

This invention relates generally to capillary electrophoretic devices. More particularly, it relates to monolithic ionic liquid-channel capillary electrophoretic devices (ILC-CED) and methods of making the same.

Conventional capillary electrophoretic (CE) devices exist for detecting ionic species in liquids. Generally, CE devices separate various ionic species in a liquid sample into separate, discrete detectable zones, wherein each zone corresponds to a single ionic species. This separation is facilitated by an electric field which pulls ions through a capillary. The migration velocity with which the ions travel through the capillary depends on the electrophoretic mobility characteristics of the particular ionic species. Thus, different ionic species travel at different speeds, and separate into discrete zones after a certain time.

A typical CE device consists of a relatively long capillary, e.g., 60 cm in length, having each end immersed in a reservoir containing a buffer solution. A high voltage power source is coupled to the tube and a detector can be coupled at either end of the tube to detect the changes in potential caused by the passage of various ionic species. A sample containing different species is introduced into the device at one end by either hydrostatic force or electromigration. The ionic species present in the sample migrate through the tube under an applied electric potential created by the voltage source. The buffer solution, usually an electrolyte, provides a source of ions for the system and facilitates movement of the ionic species through the tube by providing a background, or transportation, medium through which the species travel. The ions are detected by a light absorbing detector located near the output of the tube. Other conventional devices employ gels, such as polyacrylamide gels, instead of a liquid analyte as a background medium.

A drawback of the conventional CE devices is the high voltages necessary to move the ionic species through the capillary. Typically, the electric field created by the voltage source moves the ionic species through the tube at migration velocities sufficient to separate the species into discrete detectable zones. However, relatively high voltages, usually on the order of 10 kV to 30 kV, are required to generate this ion-separating potential. These elevated voltage levels typically necessitate shielding of the voltage source. Thus, the CE device is relatively large.

Another drawback of conventional CE devices is the relatively long capillaries that are employed. These relatively long capillaries increase the time it takes to detect selected ions that are migrating through the tube, since the ions must travel greater distances before they separate into discrete zones.

Still another drawback of conventional CE devices are the mechanical parts that are necessary to insure proper operation of the device. For example, conventional CE devices, because of their relatively long length, require a fan to circulate air around the capillary to help dissipate heat to the ambient environment. Further, the conventional CE device requires light sources and detectors to detect the ionic species present in the sample solution.

There still exists a need in the art for better electrophoretic devices that can separate ionic species into discrete detectable zones while using relatively small external voltages, and relatively small capillary tubes. In particular, a CE device that relatively easily and relatively quickly determines various ionic constituents in a liquid sample, while decreasing size and increasing sensitivity, would represent a major improvement in the art. Additionally, an electrophoretic device that is relatively easy to manufacture would also present a major improvement in the art. Moreover, a device that can be adapted for use in a relatively low cost hand-held instrument would likewise present an improvement in the art.

SUMMARY OF THE INVENTION

A monolithic capillary electrophoretic device is disclosed which includes a buried channel formed upon a semiconductor water and surrounded by an insulating material. The channel is adapted to receive a matrix liquid which functions as a transportation medium for carrying the molecules through the channel. A drive element applies a voltage between first and second electrodes positioned at separate locations in the channel. This applied voltage generates an electric field along the length of the channel that pulls the ions introduced into the channel towards at least one of the electrodes. In one preferred embodiment, ions having one polarity are attracted to the first electrode, and ions having an opposite polarity are attracted to the second electrode.

In a further embodiment, the electrophoretic device can include at least one electrical conductivity detector, and preferably two detectors, that detect when molecules pass an electrode by detecting a change in the conductivity of the channel. The device can further include first and second reservoirs that are located at opposite ends of the channel, and which hold the matrix liquid. The device can also include a part for introducing or injecting a liquid sample for analysis. The electrodes are preferably disposed at or near the reservoirs, thus facilitating the formation of an electric potential across the entire length of the channel. According to yet another embodiment, two gate electrodes supply a voltage to the channel to inhibit the adhesion of ions along the walls of the channel.

According to another aspect of the invention, the electrophoretic device of the present invention can be fabricated by depositing a sacrificial structure of silicon upon a substrate, and then covering the sacrificial structure with a first insulating material. An opening is formed in the insulating material through which an etchant is introduced. The etchant removes the sacrificial structure, thereby forming a buried channel. Electrodes are placed at different locations along the channel to produce, when energized, an electric field along the length of the channel, such that the molecular species contained in the matrix liquid migrate, under the influence of the applied electric field, along the channel at selected migration velocities. The substrate is preferably composed of an insulating material such as silicon, glass or sapphire.

The invention will next be described in connection with certain preferred embodiments. However, it should be clear that various changes and modifications can be made by those skilled in the art without departing from the spirit and scope of the invention. For example, various electronic detection units can be employed that detect the presence of various ionic species in a sample solution. Additionally, the capillary, can take various non-linear shapes, such as serpentine or double-spiral shapes.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION

Figure 1:
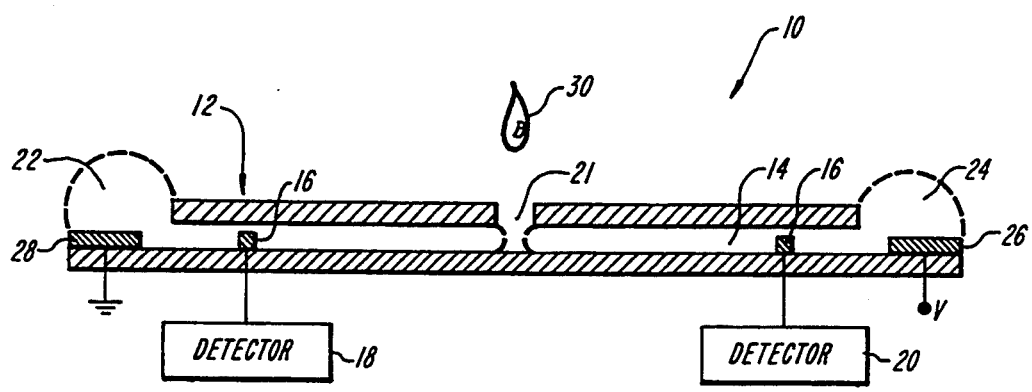
FIG. 1 is a schematic depiction of an ionic liquid-channel capillary electrophoretic device according to a preferred embodiment of the invention.

In FIG. 1, a capillary electrophoretic (CE) device 10 according to a preferred embodiment is shown which includes a housing 12 having a central capillary or channel 14, detection units 18 and 20, input voltage source V, and detection sensors 16, connected as shown. The sensors 16 are preferably impedance measuring electrodes positioned at either ends of the capillary 14.

An inlet port 21 provides an aperture within the housing 12 and extends, in a first orientation, vertically downward, communicating with the capillary 14. Preferably, the inlet port is disposed towards the middle of the housing 12. First and second reservoirs 22 and 24, respectively, are disposed at either end of the housing 12 and are in fluid communication with the capillary 14. The reservoirs contain a matrix liquid solution that functions as a transportation medium for various ionic species. The matrix solution can be any analytic solution such as water or glycerol.

An activation electrode 26 is coupled to the input voltage source V located at one end of the capillary 14, and is disposed in the second reservoir 24. A ground electrode 28 mounted at the opposite end of the capillary 14 and disposed in the first reservoir 22 is connected to ground, as shown. This bipolar arrangement, in combination, applies a voltage across the length of the capillary 14, creating an electric field within the capillary 14. This electric field is orthogonal to the capillary 14. In a preferred embodiment, each detection sensor 16 constitutes a pair of electrodes, with a complementary electrode located along the capillary wall opposite the illustrated electrode of sensor 16. The detection electrodes of sensors 16 preferably are mounted flush along the wall of the capillary 14.

A sample solution 30 containing various molecular ionic species having both cations and anions, is introduced into the capillary 14 via inlet opening 21. The sample 30 can be introduced by any suitable mechanical means. In a preferred embodiment, the size of the sample 30 is substantially greater than the fluid capacity of the capillary 14, thereby generating a constant influx of sample solution 30 into the capillary 14.

When the input voltage V is applied to the activation electrode 26, an energy potential, or electric field, is created along the length of the capillary 14. This generated electric field separates the cations and anions simultaneously into separate, detectable zones, with each zone corresponding to a particular ionic species. In the illustrated embodiment, the cations migrate to areas of lower potential, to the left in FIG. 1, and the anions migrate to areas of higher potential, to the right in FIG. 1. The detection units 18 and 20 are electrically and conductively coupled to the detection electrodes 16, and detect each zone as it passes by the electrodes 16. In a preferred embodiment, the voltage level applied to the channel ranges from about 5 V to about 50 V. Voltage sources suitable for use with the present invention are known and commercially available.

According to a preferred embodiment of the invention, each CE device contains a plurality of capillaries, e.g., on the order of ten or more parallel channels, that extend between a source electrode 26 and a drain electrode 28, (as shown in FIG. 4). Each capillary is preferably between 1 $\mu$m and 15 $\mu$m wide, between 10 nm–1 $\mu$m thick, and between 100–2000 $\mu$m long. These dimensions are significantly smaller than the dimensions of the conventional CE device.

The sensors 16 and detection circuitry 26 and 28 preferably have low resistance and low polarization voltage. In a particularly preferred embodiment, the electrodes consist of an electrically conductive plating, e.g. silver or gold, disposed over an insulating material such as polymer. The housing 12 is preferably formed using silicon chip technology, as described in further detail below.

Figure 2:
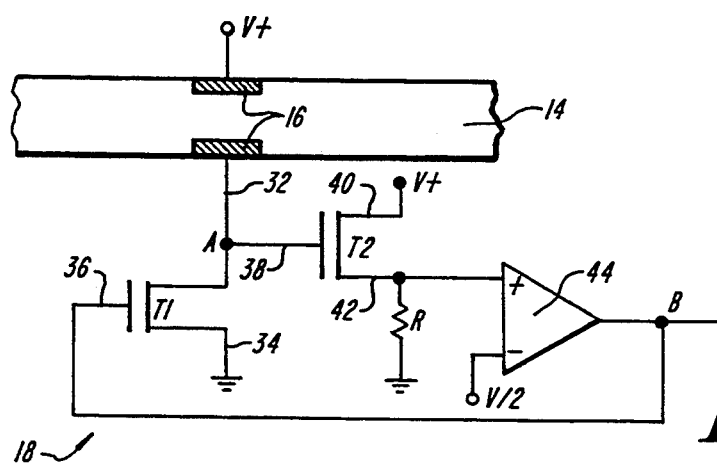
FIG. 2 is a schematic circuit diagram of the detection unit of FIG. 1 according to a preferred embodiment of the invention.

The detection units 18 and 20 detect ions migrating through the capillary 14 and that pass the electrodes of sensors 16. FIG. 2 shows a preferred detection circuit that detects ions as they pass the sensor 16 disposed in the capillary 14. The circuit consists of transistors T1 and T2, and operational amplifier 44. The transistors are preferably field effect transistors (FET). The drain 32 of transistor T1 is coupled to the electrode 16, and the source 34 is connected to ground. The transistor drain 32 is also connected to the gate 38 of transistor T2. The drain of transistor T2 is connected to a voltage source designated as V+, and the transistor source 42 is connected to resistor R and to the positive input (+) of amplifier 44. The resistor R is also connected to ground. The negative input of amplifier 44 is connected to a voltage source designated as V/2. The gate of transistor T1 is connected to the output B of the amplifier 44.

Initially, when only a few ions pass the electrode 16, the voltage at circuit connection B (output) is low. When an ionic species passes the electrode 16, changes in the conductivity of the capillary 14 couples the device to transistors T1 and T2, causing the gate 38 of transistor T2 to conduct. The current generated at the transistor source 42 divides between the resistor R and the input of the amplifier 44. Those of ordinary skill will recognize that the impedance value of R can be selected to shunt a selected level of actuating current to the amplifier 44. The amplifier 44 amplifies the voltage at the source 42 of transistor T2. Since the output of the amplifier 44 is connected to the gate 36 of transistor T1, T1 turns on, drawing current from the transistor drain 32 to the transistor source 34 keeping the voltage at circuit connection a relative constant at V/2. As one of ordinary skill will recognize, the current generated by transistor T2 adjusts the current generated by transistor T1 through the output of amplifier 44.

Although the detection circuit 18 has been described as above, other variations and modifications can be used that are apparent to one of ordinary skill in the art. For example, three transistors can be used rather than the two depicted in FIG. 2, and a source follower circuit arrangement can also be employed.

The output of the amplifier 44 can be connected to various monitoring devices and displays, such as digital display units, LED read-outs and the like.

The CE device 10 of FIG. 1 requires significantly smaller voltages to produce an electric field large enough to cause the ions to migrate through the capillary 14. By way of example, commercial CE devices consist of a capillary that is 50 $\mu$m wide and 60 cm long. A voltage of 30 kV is typically used to move ions, e.g. $Na^+$ ions and $Li^+$ ions, through the tube at a migration velocity sufficient to cause the ions to separate. As a result, the electric field produced by the voltage source along the length of the capillary is about 500 V/cm. The electrophoretic mobility characteristics of the $Na^+$ and $Li^+$ ions are $5.19 \times 10^{-4}$ $cm^2/V$ sec and $4.01 \times 10^{-4}$ $cm^2/V$ sec, respectively. Thus the $Na^+$ and $Li^+$ velocities due to the applied electric field are 0.26 cm/s and 0.20 cm/s, respectively. Assuming the electroosmotic flow velocity is negligible, the time it takes for the ions to migrate through the capillary are 231 s for $Na^+$ and 300 s for $Li^+$. Electroosmosis is the flow of solvent in an electric field applied parallel to the capillary 14. Electroosmosis can be important since it can affect the amount of time a solute resides in the capillary, and thus affects both the separation efficiency and resolution.

To achieve the same effective electric field in the CE device 10 of the present invention having a 500 $\mu$m long capillary 14, the voltage required by the device is about 25 V, a substantially smaller voltage. The time it takes for the ions to migrate through the capillary are correspondingly reduced to 192 ms and to 300 ms, respectively, assuming no electroosmotic flow.

As can be readily seen from the above example, the CE device according to the invention produces a significantly smaller device that requires significantly less voltage to create the necessary electric field, resulting in smaller migration times for the ions to travel through the capillary 14. Additionally, employing capillaries of relatively shorter length reduces the amount of heat generated by the device when exposed to the applied electric field. This reduction in heat eliminates the need to cool the capillary. These benefits allow the device to be manufactured as a small, compact unit on a semiconductor chip that can be incorporated into a handheld device.

Figure 3:
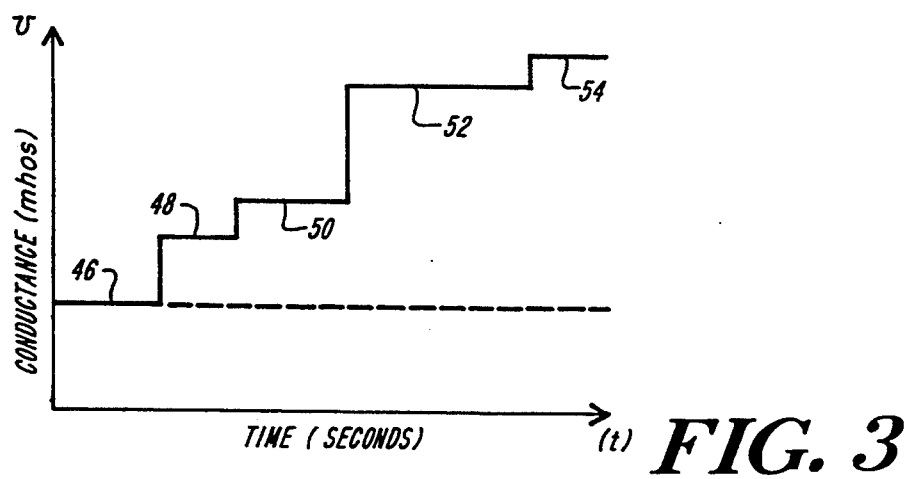
FIG. 3 is a graph illustrating the relationship between the capillary conductance and the presence of various ionic species over time.

The substantially smaller size of the capillary 14 in relation to the size of the input sample 30 forms zones of ionic species that are uniform across the cross-section of the capillary 14. FIG. 3 shows that the ionic species traveling through the device 10 have a relatively uniform cross-section across the capillary 14 when the conductivity (I/V) profile is graphed according to time. The illustrated series of step functions 46-54 represent different ionic species. The species are detected and recorded as they pass the detection electrodes 16 and detection circuits 18 and 20. The different species migrate through the capillary at different migration velocities because of different electrophoretic mobilities, and hence, pass the detectors 18, 20 at different times. This separation of the ionic species according to electrophoretic mobility characteristics creates the illustrated series of steps. This is in contrast to conventional CE devices whose graph of conductance over time resembles a spike in time, since the ionic species traveling through the capillary 14 are not uniform across the cross-section of the capillary.

The height of each step function 46-54 indicates the concentration of each ionic species present in the sample 30. The measured conductance increases each time a new ionic species is detected by the detection units 18,20 since the sample 30 operates as a continuous source of ions, thereby providing the capillary 14 with a constant and uniform supply of each ionic species. For example, the species represented by step function 46 will be present in that particular concentration (illustrated as the horizontal dashed line) for as long as the input supply of that species remains the same. As each additional species is detected by the detection units 18, 20, the concentration in the capillary of that particular ionic species increases the total amount of ions passing the detector at that time. The conductance of the capillary also depends on the particular concentration of ions in the channel since the current in the capillary is carried by both the anions and cations. The number of ions present in the capillary 14 usually depends on the applied gate voltage. For a further discussion of the basic theory behind the fabrication of ionic liquid-channel capillary devices, see *An Ionic Liquid-Channel Field-Effect Transistor*, (October 1992), *J. Electro, Chem, Soc.* V1. 139: first page, 2833 through 2840, by the present inventors, which is herein incorporated by reference.

The resolution of the various ionic species detected by the detection units 18, 20 is increased by varying the type of matrix solution present in the capillary 14. By way of example, glycerol or a glycerol/water mixture can be used in the capillary 14 instead of water. Glycerol, which is nontoxic and viscous, decreases the electrophoretic mobility characteristics of various ionic species, thereby decreasing the migration velocities of these species. The mobility of $Na^+$ and $Li^+$ ions in glycerol are $1.30 \times 10^{-6}$ cm/V s and $0.86 \times 10^{-6}$ $cm^2/V$ s, respectively, and thus are 400 and 466 times slower in glycerol than in water. The moving edges of the each zone of ionic species thus moves slower in glycerol than in water. The advantage of having the species move slower is that ions pile up at the species/glycerol interface, better defining the edges of the step functions, FIG. 3, and thus increasing resolution.

Figure 4A:
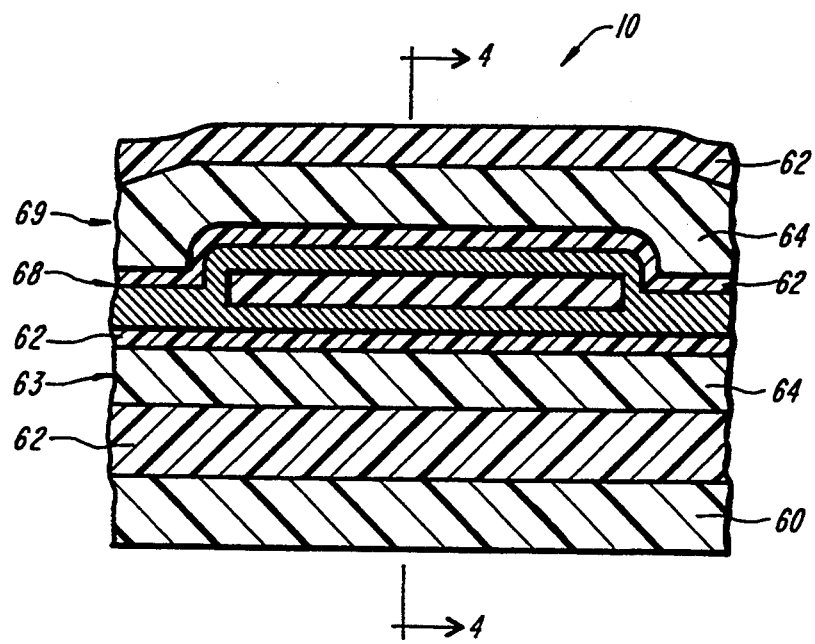
FIG. 4A is an orthogonal cross-section of FIG. 1 illustrating the different material layers of the housing according to a preferred embodiment of the invention.
Figure 4B:
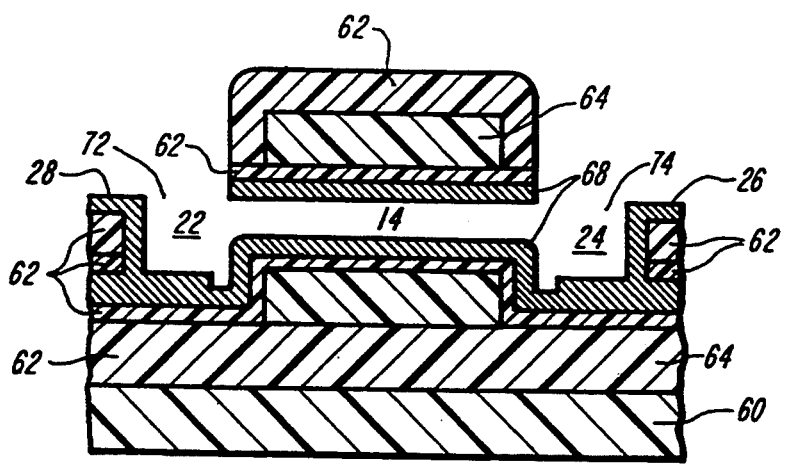
FIG. 4B is a cross-sectional view taken along line 4—4 of FIG. 4A.

FIGS. 4A and 4B illustrate the various layers and materials that are utilized to form the housing 12 of the CE device 10 of the present invention. Referring to FIG. 4A, an electrical insulating material 62 covers a substrate 60. The electrical insulator 62 is preferably silicon dioxide ($SiO_2$) and is preferably 2 $\mu$m thick. A layer of polysilicon 64, preferably phosphorus-doped polysilicon, is applied to the insulating material by a technique, such as chemical vapor deposition, and is patterned to form lower gate electrode 63. The polysilicon layer 64 is electrically and ionically insulated from the matrix liquid and the sample solution 30 by thin layers of the insulating material 62 and a layer of silicon nitride ($Si_3N_4$) 68, which is also coated on the insulating material 62 by chemical vapor deposition or like techniques. A sacrificial structure 70, such as amorphous silicon, is positioned on the silicon nitride layer 68. When more than one capillary is desired, then a series of sacrificial structures can be placed along the layer 68. An additional layer 68 of silicon nitride is formed over the structure 70, and a third layer of insulator 62 is deposited over layer 68. The layers 68 and 62 form the upper and lower halves of the capillary 14. Again, a layer of polysilicon 64 is deposited on the third insulating layer 62, forming an upper gate electrode 69, and then a fourth layer of insulator 62, preferably 1 μm thick, is deposited over the upper electrode 69. The substrate is preferably formed of an insulating material, such as silicon (semiconductor wafer), glass or sapphire. Glass and sapphire are preferably used when larger voltage levels are desired, so as to reduce the risk of a dielectric breakdown of the device materials.

The device 10 contains openings (not shown) that communicate with the sacrificial structure 70 that are formed by etching the insulating layer 62 and the silicon nitride layer 64 in the device source and drain reservoir regions 72 and 74, FIG. 4B. The etchant, preferably tetramethylammonium hydroxide, completely removes the sacrificial structure 70 to form the capillary 14 without harming the silicon nitride layer 68. Referring to FIG. 4B, contacts for the electrodes 26, 28, 63 and 69 are formed by depositing and patterning metal onto the electrodes with a liftoff process. The electrode contacts are preferably formed by coating a 10 nm thick adhesion layer of chromium with a 0.1 μm thick layer of a conductive metal, such as copper, silver, or gold.

The capillaries formed in the device 10 are preferably elongate in shape. However, whenever it is desired that the overall length of the capillary exceed the diameter of the silicon wafer, the capillary length can be increased by forming the sacrificial structure in a serpentine, spiral, or other like configuration.

A voltage source (not shown) is preferably connected between the source and drain electrodes 26, 28, as well as to the gate electrodes 63, 69. A suitable voltage applied to the gate electrodes 63, 69 relative to either reservoir repels ions that cohere to the capillary walls. During typical applications, the externally applied orthogonal electric field analyzes these ions from the capillary wall. These ions interact with the ionic species migrating through the capillary 14 that are adjacent to the capillary wall. As a result, the ions concentrated towards the center of the capillary travel at a velocity faster than the ions along the wall surface, diffusing the zone of ions. This diffusion results in a decrease in resolution.

During operation, a sample solution 30 is introduced into the capillary 14 via opening 21. The molecular species present in the solution are pulled through the capillary 14 by an externally applied orthogonal electric field. The rate at which the ions travel through the capillary depends upon the electrophoretic mobility characteristics of the ionic species. Further, positively charged ions will migrate towards the cathode and the anions will migrate towards the anode. At the ions migrate through the capillary 14, they pass either sensor 16. The detection units 18 and 20, capacitively coupled to the capillary 14, detect the passage of ions by detecting dielectric changes in the matrix liquid. The conductance of the capillary, if graphed over time, resembles a series of step functions.

The CE device 10 employs relatively short capillaries 14. This shorter length reduces the thermal effects of the applied electric field. Furthermore, a lower potential or voltage level can be applied since the relatively short capillary length does not necessitate the application of high potentials to induce the ions to migrate through the capillary.

Having described the invention, what is claimed as new and desired to be secured by Letters Patent is:

1. A monolithic capillary electrophoretic device for separating molecules in a liquid sample based on electrophoretic mobility, the device comprising:

a buried channel formed upon a semiconductor wafer and at least partially enclosed by a deposited insulating material thereby forming a monolithic structure, the channel serving as a container for a matrix liquid;

at least a first electrode and a second electrode, located at a first and a second site, respectively, along the channel;

drive means for applying a voltage between the first and second electrodes; and introduction means for introducing a liquid sample into the channel at a location between the first and second electrode sites;

whereby upon application of the voltage by the drive means, ions in the sample of one charged molecular species are attracted to the first electrode and oppositely charged molecular species are attracted to the second electrode.

2. The device of claim 1 further comprising at least one electronic detector disposed along the channel to detect the presence of molecular species by measuring the conductivity of the channel.

3. The device of claim 1 wherein the device further comprises first and second reservoir means disposed at opposite ends of the channel to provide a reservoir for the matrix liquid, and to facilitate migration of the charged species in the sample liquid.

4. The device of claim 3 wherein such of the first and second reservoir means further comprises an electrode for application of a voltage across the length of the channel.

5. The device of claim 1 further comprising at least one gate electrode for applying a voltage across the insulating material surrounding the channel, thereby repelling ions away from the walls of the channel during migration of the charged species.

6. The device of claim 1 wherein the length of the channel ranges from about 100 μm to about 2000 μm.

7. The device of claim 1 wherein the dimensions of the channel range from about 1 μm to about 15 μm wide, and from about 10 nm to about 1 μm thick.

8. The device according to claim 1 wherein the voltage applied to the channel by the drive means ranges from about 5 V to about 50 V.

9. A method of fabricating a monolithic capillary electrophoretic device for separating molecular species, the method comprising:

depositing a sacrificial structure of amorphous silicon upon a substrate;

covering the sacrificial structure with a first insulating material;

providing at least one opening in the covering insulating material;

introducing an etchant via the opening to remove the sacrificial structure to form a buried channel having a first end and a second end; and depositing at least two electrodes at different locations along the channel such that upon filling of the channel with a liquid matrix containing at least one ion species, and application of a voltage across the channel via the electrodes induces the ion species to migrate along the channel at selected migration velocities.

10. The method of claim 9 further comprising, before the step of depositing a sacrificial structure,
applying a layer of a second insulating material onto the substrate,
depositing on the second insulating material a first layer of polysilicon,
applying an additional layer of the second insulating material onto the polysilicon layer, and
covering the additional layer of the second insulating material with an another layer of the first insulating material.

11. The method of claim 10 further comprising, before the providing step, depositing on the first insulating material a second layer of polysilicon, and applying a final layer of the second insulating material onto the second polysilicon layer.

12. The method of claim 11 wherein the polysilicon layer forms gate electrodes such that an electrical charge can be imposed upon the gate electrode to repel ions from the channel walls.

13. The method of claim 9 further comprising disposing at least one electrode at the first end and at the second end of the channel, to detect the passage of the ion species by measuring the conductivity of the channel.

14. The method of claim 9 wherein the substrate is selected from the group consisting of silicon, glass and sapphire.

15. The method of claim 11 wherein the second insulating material is composed of silicon nitride.

16. The method of claim 9 wherein the etchant is tetramethylammonium hydroxide.

17. The method of claim 9 wherein the first insulating layers form gate electrodes.

18. The method of claim 17 wherein the first insulating layer is silicon dioxide.

19. The method of claim 9 wherein the length of the buried channel ranges from about 100 $\mu$m to about 2000 $\mu$m.

20. The method of claim 9 wherein the voltage applied to the channel ranges from about 5 V to about 50 V.

21. A monolithic capillary electrophoretic device for separating molecules in a liquid sample based on electrophoretic mobility, the device comprising:
a buried channel formed upon a semiconductor wafer to serve as a container for a matrix liquid, and surrounded by an insulating material;
at least a first electrode and a second electrode, located at a first and a second site, respectively, along the channel;
drive means for applying a voltage between the first and second electrodes;
introduction means for introducing a liquid sample into the channel at a location between the first and second electrode sites; and
at least one gate electrode for applying a voltage across the insulating material surrounding the channel, thereby repelling ions away from the walls of the channel during migration of the charged species;
whereby upon application of the voltage by the drive means, ions in the sample of one charge species are attracted to the first electrode and oppositely charged molecular species are attracted to the second electrode.

22. A monolithic capillary electrophoretic device for separating molecules in a liquid sample based on electrophoretic mobility, the device comprising:
a buried channel formed upon a semiconductor wafer to serve as a container for a matrix liquid, and surrounded by an insulating material, wherein the length of the channel ranges between about 100 $\mu$m and about 2000 $\mu$m;
at least a first electrode and a second electrode, located at a first and a second site, respectively, along the channel;
drive means for applying a voltage between the first and second electrodes; and
introduction means for introducing a liquid sample into the channel at a location between the first and second electrode sites;
whereby upon application of the voltage by the drive means, ions in the sample of one charge species are attracted to the first electrode and oppositely charged molecular species are attracted to the second electrode.

23. A monolithic capillary electrophoretic device for separating molecules in a liquid sample based on electrophoretic mobility, the device comprising:
a buried channel formed upon a semiconductor wafer to serve as a container for a matrix liquid, and surrounded by an insulating material, wherein the dimensions of the channel range between about 1 $\mu$m and about 15 $\mu$m wide, and between about 10 nm and about 1 $\mu$m thick;
at least a first electrode and a second electrode, located at a first and a second site, respectively, along the channel;
drive means for applying a voltage between the first and second electrodes; and
introduction means for introducing a liquid sample into the channel at a location between the first and second electrode sites;
whereby upon application of the voltage by the drive means, ions in the sample of one charge species are attracted to the first electrode and oppositely charged molecular species are attracted to the second electrode.

* * * * *